(12) United States Patent
Coroneo

(10) Patent No.: US 6,367,480 B1
(45) Date of Patent: Apr. 9, 2002

(54) METHODS FOR VISUALIZING THE ANTERIOR LENS CAPSULE OF THE HUMAN EYE

(76) Inventor: Minas Theodore Coroneo, 2 St. Paul's Street, Randwick, NSW 2031 (AU)

( * ) Notice: Subject to any disclaimer, the term of this patent is extended or adjusted under 35 U.S.C. 154(b) by 0 days.

(21) Appl. No.: 09/426,769

(22) Filed: Oct. 26, 1999

Related U.S. Application Data

(60) Provisional application No. 60/142,901, filed on Jul. 9, 1999.

(51) Int. Cl.7 .............................................. A61B 19/00
(52) U.S. Cl. ...................................................... 128/898
(58) Field of Search ........................... 623/6.11; 215/47; 606/107

(56) References Cited

U.S. PATENT DOCUMENTS 5,569,191 A * 10/1996 Meyer .......................... 604/82

OTHER PUBLICATIONS

Melles, Gerrit R.J., et al., "techniques" vol. 25., Trypan blue capsule staining to visualize the capsulorhexis in cataract surgery, pp 7–9, (Jan. 1999).*

Budavari, S., et al., eds. The Merck Index, Whitehouse Station, NJ. Merck & Co., Inc. 1996; p 1668.*

Hoffer, K.J., McFarland, J.E., J Cataract Refract Surg vol. 19, Intracameral Subcapsular Flourescein Staining for Improved Visualization During Capsulorhexis in Mature Cataracts, p 566, (Jul. 1993).*

Black, H., Ocular Surgery News, Soft–shell technique uses two kinds of viscoelastics to achieve good results, p 17, (Sep. 15, 1996).*

* cited by examiner

Primary Examiner—Corrine McDermott
Assistant Examiner—Thomas Barrett
(74) Attorney, Agent, or Firm—Foley & Lardner

(57) ABSTRACT

Use of trypan blue in the manufacture of a composition to enhance the visualisation of the anterior lens capsule of the eye during removal of a cataractous lens and lens replacement procedures is described. Also described are methods for the visualisation of the anterior lens capsule and processes for cataract treatment.

4 Claims, No Drawings

METHODS FOR VISUALIZING THE ANTERIOR LENS CAPSULE OF THE HUMAN EYE

This application claims benefit of Prov. No. 60/142,901 filed Jul. 9, 1999.

FIELD OF THE INVENTION

The present invention relates to therapeutic methods, compositions, and uses, more particularly to methods, compositions and uses associated with the eye, such as cataract treatment.

BACKGROUND OF THE INVENTION

Cataract is an exceptionally common condition affecting people of all racial groups. Cataract causes loss of visual capacity. Essentially, a cataract is an opacity of the crystalline lens, a key component of the eye's focusing system. The extent of opacity within the crysalline lens can vary, affecting the whole lens or only part thereof. The opaque region can prevent or retard the transmission of light through to the retina. Apart from affecting the capacity to visualize objects, cataracts may also scatter light, such that discomfort from sunlight and bright lights may result i.e. glare. Cataracts also affect animals, including animals such as dogs and cats.

Cataract most commonly occurs with increasing age but may occur as a congenital or genetic anomaly or in association with various diseases or certain medications. It is frequently the most common cause of decreased vision (not correctable with glasses) yet is one of the most successfully treated conditions by surgery.

The standard treatment for cataracts, is removal of the lens substance, and replacement of the cataractous human lens with an intraocular lens. Intraocular lenses are inserted into the eye in place of the removed cataractous lens, thereby improving and frequently retaining vision to normal levels.

Techniques for cataract treatment have been advanced by phacoemulsification surgery, this involving a very small corneo-limbal incision, to gain access to the lens capsule, creating an incision in the lens capsule to access the lens substance (cortex and nucleus) and removal of the lens by high frequency ultrasound and suction with irrigation. The capsule (the basement membrane which surrounds the crystalline lens) and its attachment, the zonular apparatus which suspends the lens from the ciliary body, are left largely intact, except for the anterior capsulotomy, that is the incision in the capsule through which the cataractous lens is removed and its replacement inserted. Preservation of this inert ocular structure (i.e. capsule and zonular apparatus) supplies a mechanism by which intraocular lenses can be implanted so that they do not impinge on vital structures (as occurs with angle or iris supported intraocular lenses) and thus avoids chronic complications such as uveitis, glaucoma and corneal decompensation.

During phacoemulsification surgery the anterior crystalline lens capsule is torn away to form a circular opening by which the lens material can be removed (continuous curvilinear capsulorhexis). This produces a strong capsular rim that resists tearing even when stretched—generally improving the safety margin during surgery. In extracapsular surgery, a so-called can-opener capsulotomy is performed, but the irregular edges of the capsule are prone to radial capsular extension tears which can result in loss of vitreous or the lens into the vitreous, both adverse events which frequently result in a suboptimal result and complications. Furthermore, following intraocular lens insertion, lens capsular fibrosis can cause decentration of the intraocular lens (with resultant astigmatism and lens-edge induced glare) but this occurs less frequently following capsulorhexis because the forces generated within the capsular bag are more symmetrical. Thus capsulorhexis is a critical step in achieving a good surgical result.

Visualization of the capsule, particularly the anterior lens capsule, is critical in capsulorhexis procedures. Capsulorhexis is generally performed in the presence of the red reflex, where light reflecting off the retina highlights the anterior capsule against a reddened background. Capsulorhexis is difficult in patients with dense cataracts (mature, usually white or very dense cataracts) where the red reflex is difficult to see, or simply not present. In these cases, elective extracapsular surgery is usually performed with its inherent inadequacies and difficulties. Capsulorhexis may also be difficult to perform in presence of corneal opacities (such as scars) or vitreous opacity, such as vitreous hemorrhage (for examples sometimes seen in patients with diabetes).

Various approaches have been tried to improve the success rate of performing capsulorhexis in patients with dense cataracts, or in conditions where the anterior lens capsule cannot be visualized for whatever reason. These include:

1. Using high magnification, dimming the operating theatre lights and using side illumination via a fibre-optic light source to enhance the view of the capsule. These procedures are clumsy, costly, and not particularly effective.
2. Using dyes, particularly fluorescein to stain the capsule and allow it to be highlighted against the unstrained underlying opaque lens fibres. Such dyes are difficult to use in the eye, they diffuse rapidly into the lens and cornea and require fitting of the operating microscope with appropriate filters to optimize visualization. Possible toxic effects of dyes also arise.
3. Haemocolouration of the capsule with the patients own blood.
4. Development of specialized cutting techniques, such as radiofrequency cutting devices, which require expensive additional instrumentation and have been shown to produce circular holes in the anterior lens capsule of inferior strength to the standard capsulorhexis.

None of these techniques have found widespread use.

There remains a distinct mean for methods, compositions and uses which enable ready visualization of the anterior lens capsule, so that capsulorhexis can be carried out so as to allow cataract removal and replacement with an intraocular lens in a safe, efficient, and cost-effective manner.

SUMMARY OF INVENTION

This invention is concerned with methods, compositions and uses for the visualization of the anterior lens capsule during cataract removal and lens replacement procedures. The invention is based on the surprising finding that the vital dye trypan blue can be readily used to stain the anterior lens capsule free of disadvantages associated with other dyes.

In accordance with a first aspect of this invention there is provided use of trypan blue in the manufacture of a compositions for the visualization of the anterior lens capsule of the eye during removal of cataractous lenses and lens replacement procedure.

In accordance with another aspect of the invention there is provided a method for visualising the anterior lens capsule of a human subject which comprises instilling into the anterior chamber of the eye a trypan blue solution of trypan blue dissolved in an ocularly compatible vehicle.

In accordance with a further aspect of this invention there is provided a method for the visualization of the anterior lens capsule which comprises introducing trypan blue into the anterior chamber of the eye following the addition of a viscoelastic substances into the anterior chamber of the eye to confine the trypan blue to the anterior capsular area.

In accordance with a further aspect of this invention there is provided a method for the visualization of the anterior lens capsule during the capsulorhexis procedure, which comprises filling the anterior chamber of the eye with viscoelastic substances of different viscosities, introducing a trypan blue solution comprising about 0.05% to 3% w/w trypan blue solution below the viscoelastic substances for a time sufficient to stain the anterior lens capsule, removing from the anterior chamber of the eye the excess trypan blue and viscoelastic substances, re-introducing fresh viscoelastic substances into the anterior chamber of the eye, and thereafter carrying out capsulorhexis, lens removal and replacement with an intraocular lens.

In a still further aspect this invention relates to a method for cataract treatment which comprises filling the anterior chamber of the eye with viscoelastic substances, introducing a trypan blue solution comprising about 0.05% to about 3% w/w trypan blue below the viscoelastic substance for a time sufficient to stain the anterior lens capsule, removing from the anterior chamber of the eye the excess trypan blue and viscoelastic, re-introducing viscoelastic substances into the anterior chamber, and thereafter carrying out capsulorhexis, lens removal and lens replacement with an intraocular lens.

DETAILED DESCRIPTION OF THE INVENTION

This invention utilizes trypan blue in methods, compositions and uses particularly in the replacement of cataract affected lenses. Trypan blue has surprisingly been found to specifically enable visualization of the anterior lens capsule by the fact that it preferentially stains the anterior lens capsule and this can be detected by simply using the standard illumination system of the operating microscope used in cataract surgery. More specifically, the anterior capsule having been readily visualized can be subjected to capsulorhexis and then cataract extraction can proceed as in a routine case.

In accordance with the first aspect of this invention there is provided use of trypan blue in the manufacture of a composition for the visualization of the anterior lens capsule of the eye during removal of cataractous lenses and lens replacement procedure. The cataractous lenses may be human lenses, or lenses of animals, such as domestic animals. The composition is preferably provided as a two part composition, the first part comprising trypan blue powder and the second part comprising an ocularly compatible solution wherein the trypan blue is mixed with the solution to give a composition for instillation into the eye.

Trypan blue is a widely available dye, which has been used in medical applications for many years. It is FDA approved for in-vivo and in-vitro uses. Trypan blue is preferably freshly prepared at the time of use. This may be conveniently achieved by a two chamber unit containing dry trypan blue (in powder form) in one chamber, and an ocularly compatible solution in the other chamber, for example separated by openable barrier means such as a rubber stopper, such that on mixing after opening the barrier means an ocularly acceptable composition is prepared which can be introduced into the anterior chamber so as to stain and allow subsequent visualization of the anterior lens capsule.

As an alternative, trypan blue solutions may be provided. Generally, trypan blue solutions contain trypan blue in an amount of 0.05% to 3% w/w, more preferably 0.1% to 1.5% w/w, still more preferably 0.1% w/w.

Compositions of trypan blue in an ocularly acceptable carrier may be prepared, such as those comprising trypan blue from 0.05% to 3% w/w, according to standard methods. Such solutions may be stored, for example, according to established procedures for storage of solutions for medical use. Compositions are generally isotonic. For introduction into the eye, the solutions are sterile, buffered and free of particulate material. Suitable solutions include w/w solution physiological saline. Using the facilities of the Prince of Wales Hospital Pharmacy we have manufactured 0.1% solutions of trypan blue shortly before use in patients. Under sterile conditions trypan blue may be dissolved in Balanced Salt Solution and filtered through a 0.22 micron filter. By testing a number of different concentrations of the dye in the porcine eyes we concluded that this a 0.1% w/w solution was a preferred concentration from the perspective of cost, and performance. Having said this trypan blue solutions in an amount from about 0.05% w/w to 3% w/w may be used.

The word "composition" is used herein in two senses, the first to describe two part composition comprising as a first part a trypan blue powder and as a second part an ocularly compatible solution. The parts may be separated by an operable barrier means. In the other sense "composition" is used to describe the solution resulting from the mixing of trypan blue powder with an ocularly compatible solution to give the solution for instillation into the eye.

In accordance with another aspect of the invention there is provided a method for visualising the anterior lens capsule of a human subject which comprises instilling into the anterior chamber of the eye a try-pan blue solution of trypan blue dissolved in an ocularly compatible vehicle.

In a further aspect of this invention there is provided a method for the visualization of the anterior lens capsule which comprises introducing trypan blue into the anterior chamber of the eye following the addition of viscoelastic substances into the anterior chamber of the eye. Trypan blue is used to visualize the anterior lens capsule by introducing the trypan blue into the anterior capsule of the eye via a corneo-limbal incision in the wall of the eye through which a probe can be introduced. Trypan blue solutions generally comprise from 0.05% w/w to 3% w/w trypan blue. After an appropriate small corneo-limbal incision is made, a probe is used to introduce the viscoelastic substances into the anterior chamber so as to prevent collapse of the anterior chamber and allow access to the lens capsule during the procedure. The trypan blue solution is introduced using the probe at the base of the viscoelastic layer, whereafter staining of the anterior lens capsule takes place. Removal of unbound trypan blue and the viscoelastic substances then follows. After re-introduction of fresh viscoelastic substances into the anterior chamber, the anterior capsule is readily visible and may be subject to capsulorhexis, that is, the formation of a circular opening. Routine phacoemulsification of the cataractous lens can then take place, with removal by phacoemulsification followed by insertion of an intraocular lens into the lens capsular bag. Following this, the viscoelastic substances are removed by suction and the probes used to carry out this process withdrawn from the eye.

The anatomy of the eye has been is well established and is comprehensively described, for example, in Duke-Elder S and Wybar K C. System of Ophthalmology, Volume II That Anatomy of the Visual System. Henry Kimpton, London 1961 and Bron A J, Tripathi R, Tripathi B. Wolff's Anatomy of the Eye and Orbit, Lippincott-Raven, 1998, which is incorporated herein by reference. For the present purposes the eye includes a pupil margin defined by the iris which regulates access of light to the lens. Pupil dilation caused by contraction of the iris dilator muscle defines a pupil margin and an area without the pupil overlying the lens.

The nature of the viscoelastic substances is not critical to this invention. A preferred technique involves using a more viscous viscoelastic (such as Healon G V, Pharmacia & Upjohn) agent at the pupil margin and a less viscous agent (Healon) within the pupil, as this serves to minimize leakage of trypan blue away from the central anterior lens capsule (in one case too much trypan blue was instilled, staining the posterior lens capsule and obscuring the view during the rest of the procedure). Such compositions are widely used in relation to other ocular treatments and surgery and these materials are commercially available from many suppliers of a grade and purity sufficient for ocular use. There are numerous other preparations of this type including Duovisc Viscoelastic System (Alcon), AMO Vitrax (Allergan) and Ocucoat (Storz).

In accordance with another aspect of this invention there is provided a method for the visualization of the anterior lens capsule during capsulorhexis procedures, which comprises filling the anterior chamber of the eye with viscoelastic substances, introducing a trypan blue solution comprising about 0.05% w/w to 3% trypan blue below the viscoelastic substance for a time sufficient to stain the anterior lens capsule, removing from the anterior chamber of the eye the excess trypan blue and viscoelastic, re-introducing viscoelastic into the anterior capsule, and thereafter carrying out capsulorhexis, lens removal and replacement with an intraocular lens.

There have been certain techniques described which relate to carrying out capsulorhexis processes which includes filling the anterior chamber with air. Such techniques are suboptimal as air contact causes corneal endothelial cell damage and may result in corneal edema.

Generally, the pupil is dilated prior to the process of this invention, utilizing well-described agents for pupil dilation. Topical and peribulbar anaesthetic is conventionally used to anaesthetise the eye. Two very small corneal-limbal incisions are made on either side of the eye through which probes are inserted for carrying out the process of this invention. Through these very small incisions, a fluid introduction suction probe is introduced in order to add viscoelastic agents prior to trypan blue, and to remove solutions added to the eye. A needle for capsulorhexis and a phacoemulsification probe can be readily inserted through the other incision. An intraocular lens can be inserted readily through the incision, which has been used for the phacoemulsification probe. Incisions are generally self-sealing and require no suture, or on some occasions only a single suture.

According to a still further aspect of the invention there is provided a process for cataract treatment which comprises filling the anterior chamber of the eye with viscoelastic substances, introducing a trypan blue solution comprising about 0.05% w/w to about 3% w/w trypan blue below the viscoelastic substance for a time sufficient to stain the anterior lens capsule, removing from the anterior chamber of the eye the excess trypan blue and viscoelastic substances, re-introducing viscoelastic substances into the anterior capsule, and thereafter carrying out capsulorhexis, lens removal and replacement with an intraocular lens.

This invention in its various aspects is applicable to cataractous lenses of humans and animals, for example, dogs and cats.

This invention will now be described with reference to the following examples.

EXAMPLE 1

Patient A

This lady was legally blind on presentation and the cause of her visual deficit was mature (white) cataract. It was anticipated that the capsulorhexis phase of her surgery would be difficult because of poor visualization of the lens capsule against the white lens substance. She underwent routine cataract surgery with the exception that trypan blue was used to stain the anterior lens capsule for each procedure (carried out some weeks apart). Healon GV was instilled into the anterior chamber at the pupil margin; the Healon instilled in the middle of this ring of Healon GV, so that the less viscous Healon covered the anterior lens capsule. 0.1% trypan blue was the injected under the Healon and allowed to remain in contact with anterior capsule for approximately thirty seconds. Typically up to 0.1 ml of the trypan blue solution was used. Capsulorhexis was the performed routinely, the anterior lens capsule stained blue was in sharp contrast to the underlying cataractous lens substance. The surgical result was excellent with a return to normal levels of visual acuity. Follow up to eleven months has revealed no adverse effects from the procedure.

Patient B

This patient had poor vision due to corneal scarring. Although ultimately a corneal graft will be required, it was felt that her cataract was contributing to the visual deficit. As there is a long waiting time for corneal graft material and because it was felt that staging the procedures instead of carrying out cataract as well as corneal graft surgery at the same time would be safer, cataract surgery was carried out with the aid of trypan blue. Not only did trypan blue staining aid in the performance of the capsulorhexis, it made the remainder of the procedure easier to perform because the plain of the anterior capsule (the remaining anterior capsule stays blue during the procedure) could be identified through the relatively opaque cornea, thereby acting as a landmark. The patient had a significant improvement in vision following a safe cataract extraction.

Patient C

This patient had been rendered legally blind by the ocular complications of diabetes. Apart from cataract he had retinal disease and vitreous hemorrhage. To treat his retinal disease it was first necessary to carry out cataract extraction. We anticipated that this would be difficult because the vitreous hemorrhage would obscure light reflecting back from the retina during cataract surgery (the red reflex). Again trypan blue assisted both performing the capsulorhexis as well as providing a landmark during the remainder of the operation. The procedure was performed uneventfully and the patient went on to have vitreo-retinal surgery.

Every capsulorhexis specimen was submitted for histopathological examination. This confirmed that trypan blue stains the anterior half of the capsule but does not penetrate into the lens, thus allowing a sharp contrast between stained capsule and unstained underlying cataractous lens material.

We have used trypan blue in 31 cases as of Jun. 24, 1999. The longest follow-up has been eleven months. We have seen no adverse reactions, which could be attributed to use of trypan blue.

Throughout this specification and the claims which follow, unless the context requires otherwise, the word "comprise", or variations such as "comprises" or "comprising", will be understood to imply the inclusion of a stated integer or step or group of integers or steps but not the exclusion of any other integer or step or group of integers or steps.

What is claimed is:

1. A method for the visualization of an anterior lens capsule of a living human subject, comprising instilling into the anterior chamber of an eye a solution of trypan blue in an ocularly compatible vehicle followed by the addition of a viscoelastic.

2. The method for visualization of the anterior lens capsule during capsulorhexis procedures according to claim 1, which comprises filling the anterior chamber of the eye with the viscoelastic substance, introducing the trypan blue solution comprising about 0.05% w/w to 3% w/w trypan blue below the viscoelastic substance for a time sufficient to stain the anterior lens capsule, removing from the anterior chamber of the eye the excess trypan blue and viscoelastic substance, re-introducing the viscoelastic substance into the anterior capsule, and thereafter, carrying out capsulorhexis, lens removal, and replacement with an intraocular lens.

3. The method according to claim 1, wherein viscoelastic substances of differing viscosities are introduced into the eye, a less viscous substance being introduced over the lens capsule, and a more viscous substance being introduced at the pupil margin of the eye so as to minimize leakage of trypan blue from the anterior lens capsule.

4. A method for cataract treatment which comprises filling the anterior chamber of an eye with a viscoelastic substance, introducing a trypan blue solution comprising about 0.05% w/w to 3% w/w trypan blue below the viscoelastic substance for a time sufficient to stain the anterior lens capsule, removing from the anterior chamber of the eye the excess trypan blue and viscoelastic substance, re-introducing the viscoelastic substance into the anterior capsule, and thereafter, carrying out capsulorhexis, lens removal, and replacement with an intraocular lens.

* * * * *